United States Patent [19]

Thompson

[11] 4,055,906
[45] Nov. 1, 1977

[54] AUTOMATED INTERROGATING APPARATUS

[75] Inventor: Francis T. Thompson, Murrysville, Pa.

[73] Assignee: Westinghouse Electric Corporation, Pittsburgh, Pa.

[21] Appl. No.: 676,180

[22] Filed: Apr. 12, 1976

[51] Int. Cl.² .................................. G09B 7/08
[52] U.S. Cl. .................................. 35/9 A
[58] Field of Search .............. 35/5, 6, 8 R, 9 R, 9 A, 35/48 R; 235/50 R, 51; 340/172.5

[56] References Cited

U.S. PATENT DOCUMENTS

| 3,528,181 | 9/1970 | Arbon et al. | 35/9 A |
|---|---|---|---|
| 3,541,699 | 11/1970 | Baker | 35/9 A |
| 3,628,255 | 12/1971 | Golden | 35/9 E |
| 3,629,956 | 12/1971 | Thomas et al. | 35/9 A |
| 3,689,930 | 9/1972 | Strickland | 35/8 R |
| 3,735,503 | 5/1973 | Dow et al. | 35/9 A |

Primary Examiner—Richard C. Pinkham
Assistant Examiner—Vance Y. Hum
Attorney, Agent, or Firm—D. F. Straitiff

[57] ABSTRACT

An automatic self-administered interrogating apparatus that projects a series of film-frame-recorded images onto a rear projection screen. At least many of such images simultaneously present to the viewer both a question and a list of multiple choice answers, any or all of which answers may be selected by actuation of respective response buttons before a new question-answer image is brought into view on the screen. Each question has a serial number that is recorded together with the several answers, and each answer is coded on the basis of branching logic to control the number of film frames to be advanced for presentation of the next question-answer image. A selection device is included for determining which of the several film advancement codes is honored when the choice of answers necessitates such selection.

3 Claims, 5 Drawing Figures ature frame can be recorded in binary form as an array 12 of
AUTOMATED INTERROGATING APPARATUS

BACKGROUND OF THE INVENTION

1. Field of the Invention

Automatic self-administered interrogating apparatus of the visual type.

2. Description of the Prior Art

There are known in the art numerous forms of self-administered interrogation apparatus which employ a film projector for the presentation of question-and-answer material and which provide for selection of one of a number of answers that appear together on the screen. After such choice of the one answer, the film is advanced to present another question and answer group, where again one of several answers is selected. This technique can be advantageous where it is employed in connection with teaching, as often has been the case in the not too distant past, but it may introduce some difficulty if employed on a non-teaching purely interrogating-only manner, due primarily to loss of context which can have a tendency to occur.

SUMMARY OF THE INVENTION

The present invention, in providing for response to any or all of a number of multiple-choice answers that appear together on the screen, before the new question-answer image is presented, enables such selection to be made in the context of the several answers appearing together. It also tends toward more efficient use of apparatus and of the user's time.

DESCRIPTION OF A PREFERRED EMBODIMENT

Figure 1:
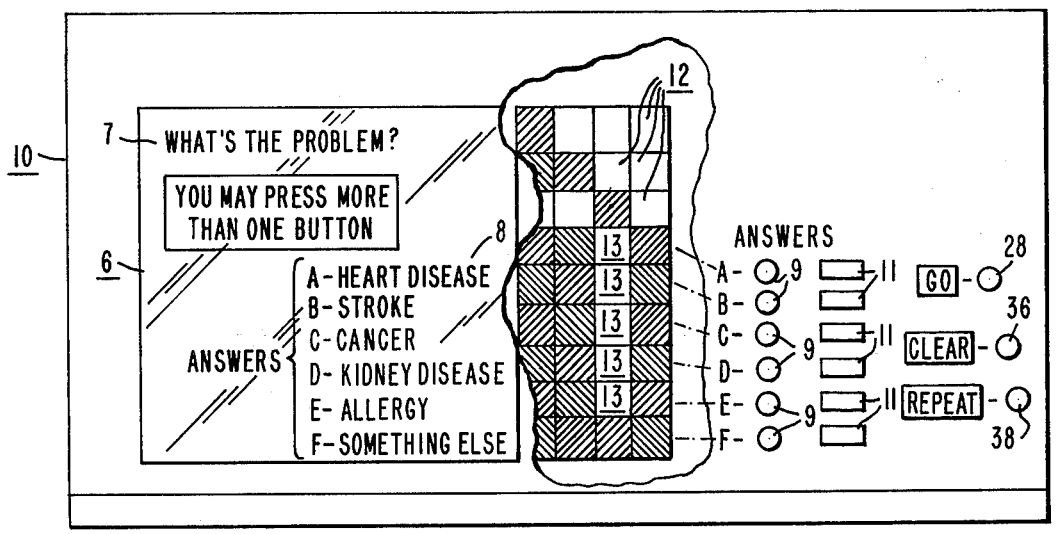
FIG. 1 is a front elevation view of a cabinet containing the interrogating apparatus of the present invention.
Figure 2:
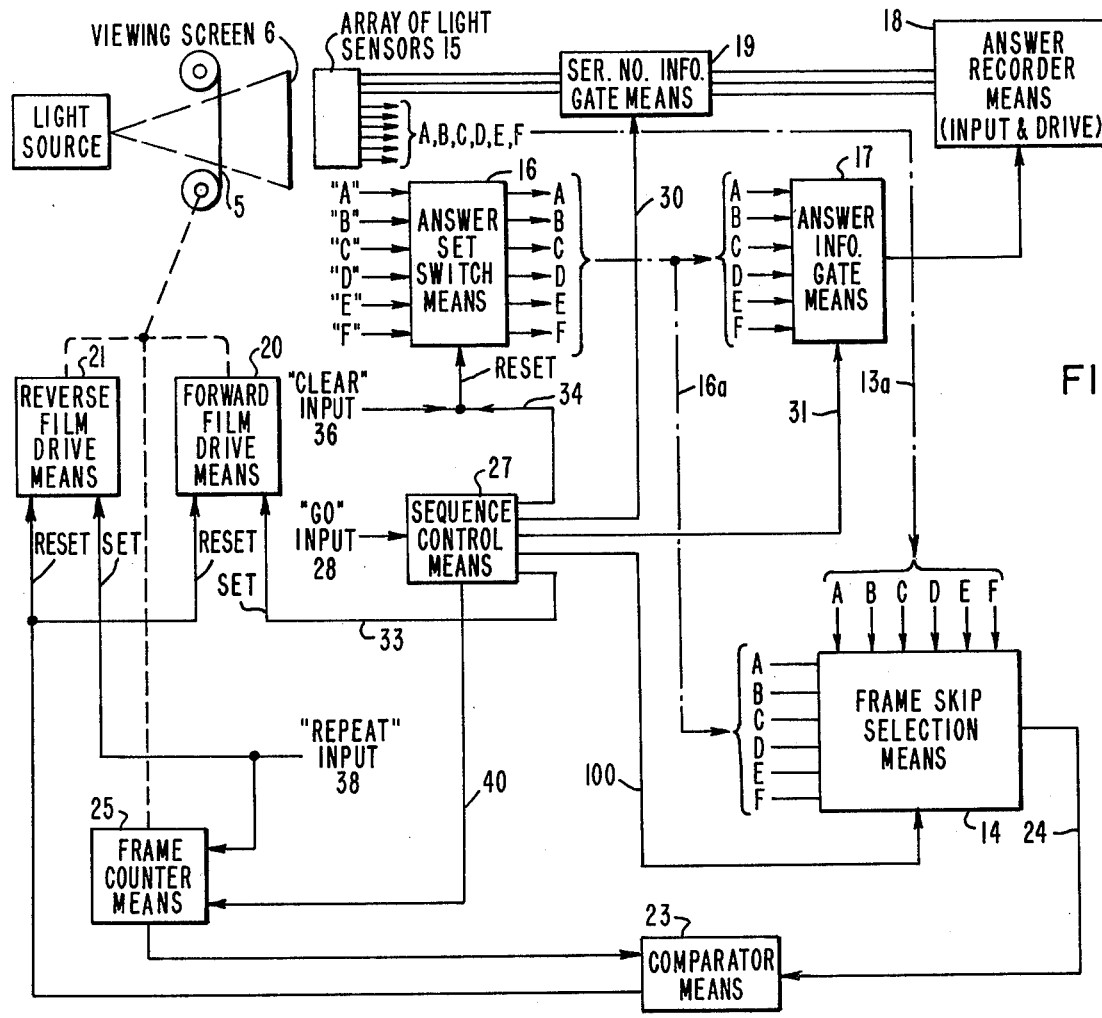
FIG. 2 is a block diagram of the present invention as embodied in a preferred form in affiliation with the housing of FIG. 1; and, FIGS. 3, 4, and 5 are block diagrams of three different alternate exemplifications, respectively, of a logic circuit suitable for use in the system of FIG. 2 to control film frame advancement.

Referring to FIGS. 1 and 2 in the drawings, the interrogating apparatus of the present invention includes a film strip 5 having a series of question-and-answer image frames extending longitudinally for selection and projection of question-and-answer images onto the back of a translucent back-lighted front-viewed screen 6. Many, if not all of the image frames from the film strip 5 are in the format of the type shown on the screen 6 in FIG. 1, where a question 7 appears together with a list of possible answers 8 that are identified by the capital letters "A" to "F", or other suitable identification markings. According to features of the present invention, any one, several, or all of the possible answers "A" to "F" may be selected by the person being interrogated, "interrogee," by pressing any one, several, or all push buttons 9 identified by letters "A" to "F" and arranged in vertical column under the legend "ANSWERS" on the front of the cabinet 10 in FIG. 1, and any such multiple answers are recorded responsively to such answer-button-pushing while only the one image frame is on display on screen 6. An indicator light 11 for each push button is activated when its respective button 9 has been pushed. A serial number for identification of the question being answered also is recorded along with the selected answers to assist in avoiding confusion when such answers are later extracted from the recording means. The serial number for any given film image frame can be recorded in binary form as an array 12 of black and white squares at one side of the question-and-answer image projected onto the screen 6, to be read by an array of light sensors 15, FIG. 2.

According to another feature of the present invention, each answer "A" to "F" has a binary-code black-and-white four-bit horizontal array 13 to indicate the number of image frames to be skipped when the film 5 is next advanced. In the exemplification of FIG. 1, the black squares indicate a binary zero (0) and the white squares a binary one (1). Answers "A" through "E" in the image depicted in FIG. 1 are binary coded 0010 to represent a frame skip of two, while answer "F" is coded 0000 to represent a frame skip of zero. Since any one, several, or all answers "A" to "F" may be selected, the apparatus includes a means 14 to determine which one of the answer skip-frame codes is to be honored for control of the next film advance. means 16 accordingly. The means 16 set by the answer buttons pushed may be in the form of an array of flip flops that become set according to answer button actuation. Upon enablement of a gate means 17, push-button-selected answer information from the switch means 16 is entered into a recorder means 18. A gate means 19 controls entry of a reading of the frame serial number of the array 12 by the sensors 15 into such means 18.

To control the advancement of the film strip 5 either forward or in reverse according to operation of drive means 20 or 21, respectively, the selected-answer codes representing frames to be skipped are picked off from the output 24 of a means 14 for determining the number of image frames to be skipped, based on the serial branching logic programmed into such answers. Means 14 operates to output a number representing, for example, the lowest one among such answer-selected codes appearing at its input. Such lowest-number output 24 becomes fed to a comparator means 23 and effectuates appropriate termination of frame-movement-operation of one or the other of the drive means 20 or 21 upon satisfaction of a nulling count from a frame counting means 25 responsive to operation of either film drive means.

To assure that the several gate means operate in the proper order for suitable operation of the apparatus, a sequence control means 27 is made to respond to a "Go" input 28 controlled by push button at the front face of the cabinet 10. After all answers are completed by selective operation of the push buttons 9, the "Go" push button 28 may be actuated to effectuate the control means 27 for sequentially delivering respective control signals: enabling, via a communication 30, the gate means 19 for entry of the film frame serial number in code form into the recorder means 18; enabling, via a communication 31, the gate means 17 to enter the selected-answer information from the switch means 16 into the recorder means 18; via a communication 40, resetting frame counter means 25; via a control communication 100, effectuating the frame-skip-number-determining means 14; effecting starting of the forward film drive means 20 via a communication 33; and, via a communication 34, effecting resetting of the answer-set switch means 16.

At any time, actuation of a "Clear" push button 36 at the front of the cabinet 10 also effects a reset of the answer-set-switch means 16, and actuation of a "Repeat" push button 38 resets frame counter means 25 and starts operation of the reverse film drive means which continues until terminated by the comparator means 23 when satisfied that the required number of frames as designated by output 24 have been backed up for realization of arrival at the previous question.

Figure 3:
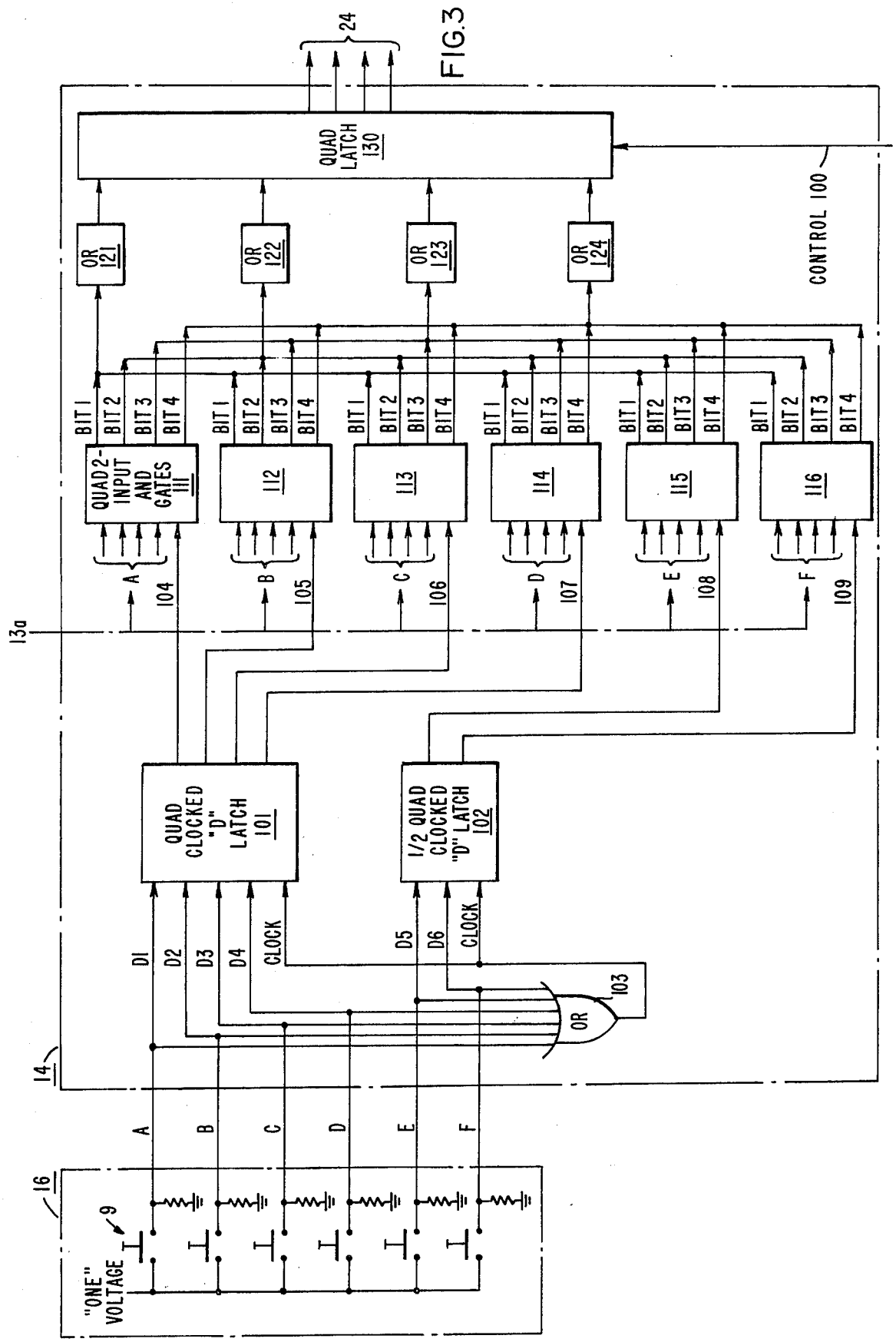
Figure 4:
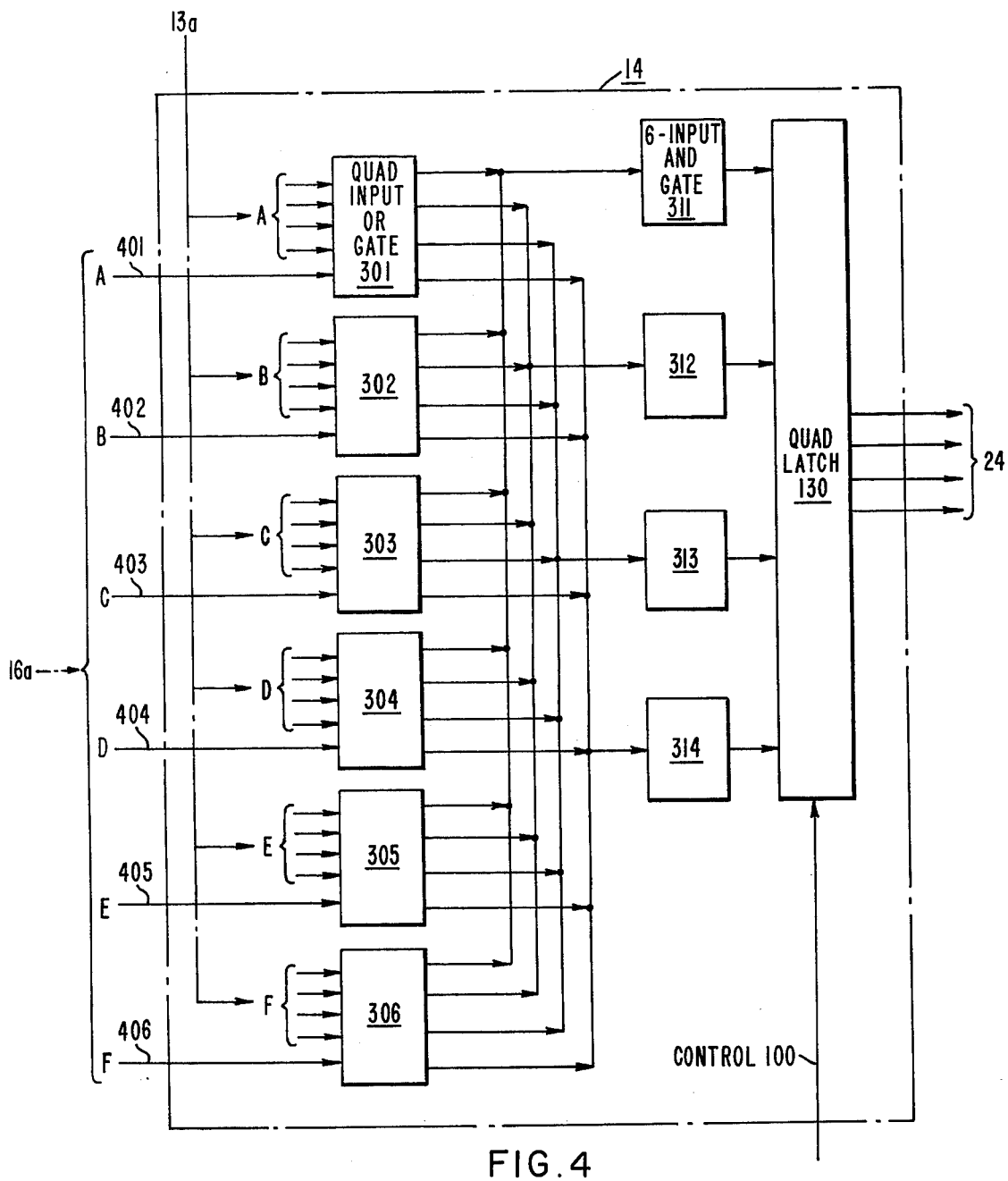
Figure 5:
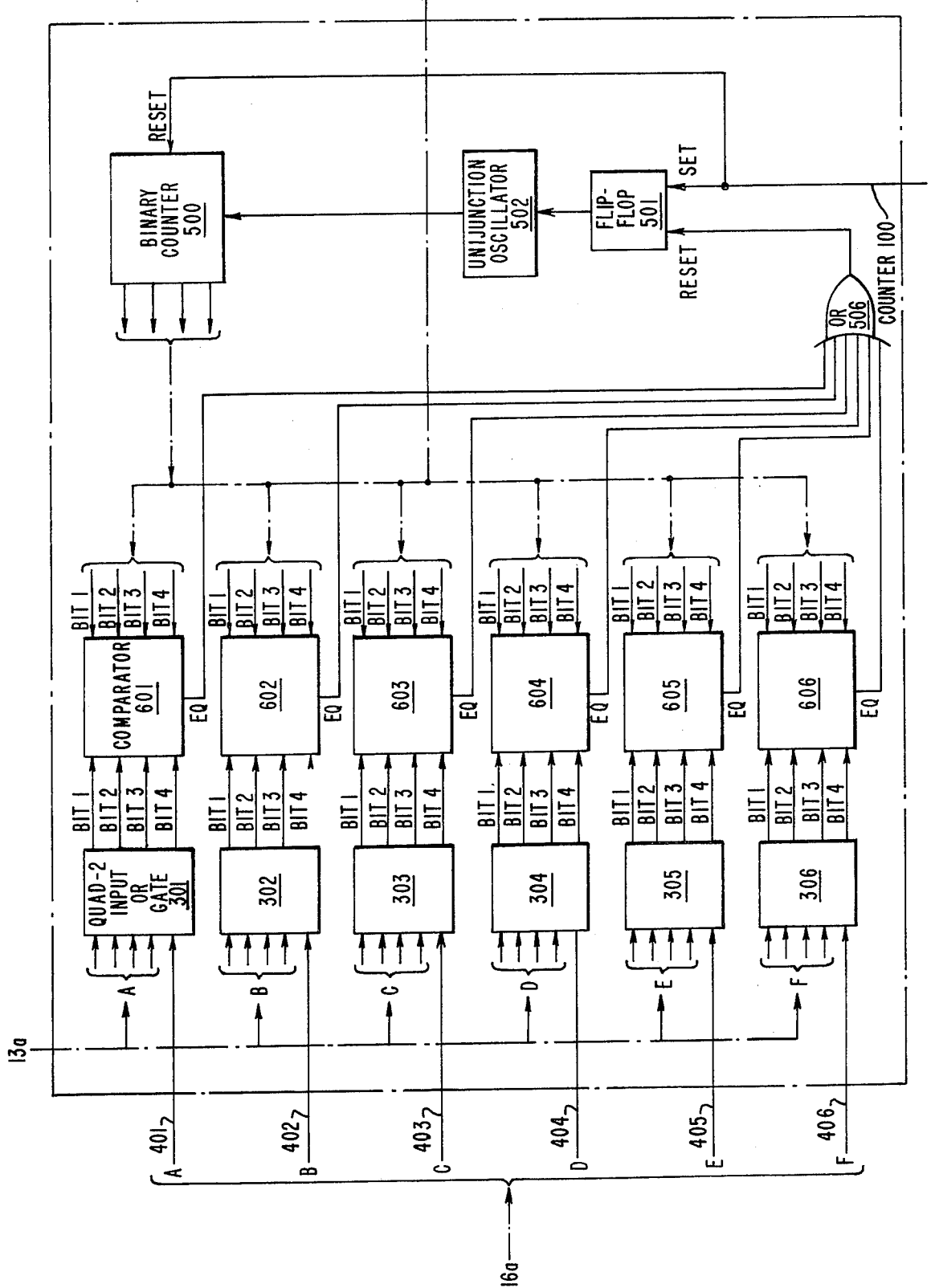

The logic circuitry embodied in the means 14 for determining the number of film frames to be skipped at each successive film advancement can take one of the several versions depicted in FIGS. 3 to 5, for example. The exemplification of FIG. 3 is based on honoring the last answer entry. That of FIG. 4 is based on a zero dominate logic, and that of FIG. 5 is based on search for the lowest answer code number among those selected by the interrogee.

Referring to FIG. 3, the frame skip set means 14 based on last answer entry logic includes four inputs D1 to D4 of a Quad Clocked "D" Latch 101 receiving the direct output of the answer buttons 9, selections A through D, and two inputs D5 and D6 of one-half of a Quad Clocked "D" latch 102 in receipt of the direct output from answer button selections E and F; which latches correspond to the monolithic silicon integrated circuit CD4042 in the RCA databook SDD-203C on COS/-MOS Digital Integrated Circuits. The clock signal for the latches 101 and 102 is obtained from a six-input OR gate 103 fed by the answer button outputs A through F. Each time a button 9 is pushed, a clock signal is obtained from the OR circuit 103 and the "ONE" signal from the pushed button is stored in the appropriate latch of quad latches 101 or 102, and all of the other latches of 101 and 102 are set to "ZERO". When the interrogee has depressed his final answer button, the corresponding latch output, Q6, for example, is a "ONE" and all other latch outputs, Q1 to Q5, are "ZERO". The same holds true for any other last-answered output, such as Q3, which will be a "ONE", and all other outputs Q1, Q2 and Q4, Q5, and Q6 will be "ZERO."

The last entry "ONE" output, Q6 or Q3, for example as above, is applied to a common input 109 or 106, respectively, of each of four AND gates in a respective one of six Quad 2-Input AND Gates 111 to 116 that gates the four-bit array code corresponding to answer F or answer C to four OR gates 121 to 124 respective to the four bits of the answer code. The remainder of the AND gates not representing the last-entry answer each will output four ZEROS, so that the four OR gates 121 to 124 are influenced only by the last-entry answer code, F or C by example chosen above, and establish outputs that collectively represent such last-entry answer code for determining the number of film frames to be skipped at next film advance. This code number is stored in a quad latch 130 upon receipt of a control signal from the clock input 100. The quad latch provides a four-bit binary output signal 24.

Referring to FIG. 4, in the frame skip set means 14 based on zero dominant logic the outputs A to F of the answer set switch means 16 that are selected by the interrogee appear in lines 401 to 406, respectively, as ZEROS, while the answer outputs corresponding to those not selected are in the ONE state. Each of the answer signal lines 401 to 406 is arranged to be one of the two inputs to each of four 2-input OR gates of a respective Quad 2-Input OR Gate having a four-bit answer-code entry as the other input. Six of such Quad 2-Input OR Gates, 301 to 306, have answer lines 401 to 406 as their one input, respectively, and four-bit answer code lines A to F as their second input, respectively. The output, Bit 1 to Bit 4, of each of the Quad gates 301 to 306 that corresponds to the push-button selected answers are replicas of the four-bit answer code at its one input resultant from a reading by the light sensor array 15 of FIG. 2. The outputs of the non-selected-answer ones of the OR Gates 301 to 306 are all ONES.

All Bit 1 outputs from the Quad OR Gates 301 to 306 are connected to a respective 6-Input AND Gate 311. All Bit 2 outputs from such OR Gates input to a 6-Input AND Gate 312, and Bits 3 and 4 from such Gates input to 6-Input AND Gates 313 and 314, respectively. The output of AND Gate 311 is a ONE only if all the selected answer four-bit codes have a ONE value at Bit 1. If any of the selected answer four-bit codes is ZERO at Bit 1, the output from Gate 311 will be ZERO. The same holds true for the outputs of the Bit 2, Bit 3, and Bit 4 AND Gates 312 to 314, respectively. From this it will be seen that the input ZERO bits dominate, and the four outputs from the four AND Gates 311 to 314 are stored in a Quad Latch 130 when a clock signal ONE appears in line 100 from the Sequence Control Means 27 of FIG. 2.

In the example of FIG. 1, if answer F is selected together with any or all of answers A through E, the ZERO bits corresponding to answer F dominate and therefore the skip code stored in latch 130 will be 0000, four ZEROS. As a result, no frames will be skipped and the film strip will be advanced to the next adjacent frame. If F had not been selected, the latch 130 code would have been 0010, a binary two, and two frames would be skipped.

In using this ZERO-dominant coding method, the combination of skip codes used together must be carefully chosen. The 0000 code may be used with any other code. However, the 0001 code, decimal one, can be used with ZERO and odd-decimal skip codes only. The rule that needs to be followed is that the selection of the ZERO bits in any combination of selected answer codes must not produce a latch 130 code having a lower decimal value than the smallest decimal value of the selected answer codes.

Referring to FIG. 5, in the exemplification of a Frame Skip Set Means 14 based on lowest number search, the answer set switch means 16, outputs A through F, lines 401 through 406, are fed as inputs to means 14. All such outputs which were selected by the interrogee will be in the ZERO state, while the outputs corresponding to not-selected answers will be in the ONE state. Each of the answer signal lines 401 to 406 is arranged as one of two inputs to each of four 2-input OR gates of a respective Quad 2-Input OR Gate having a four-bit answer code entry as the other input. As in the FIG. 4 exemplification, six of such Quad 2-Input OR Gates, 301 to 306, have the answer lines 401 to 406 as their one input, respectively, and four-bit answer code line arrays A to F as their second input, respectively. The output, Bit 1 to Bit 4, of each of the Quad OR gates 301 to 306, that corresponds to the push-button selected answers are replicas of the four-bit answer code at its one input resultant from a reading by the light sensor array 15 of FIG. 2. The outputs of the non-selected-answer ones of the OR Gates 301 to 306 are all ONES.

Following the pushing of GO button 28, sequence control means 27 applies a ONE pulse signal on control line 100 which resets a binary counter 500 to 0000 and sets a flip flop 501 to enable a unijunction oscillator 502. If any of the outputs of OR Gates 301 to 306 are 0000, an equality signal of binary value ONE is generated by a corresponding four-bit comparator, 601 to 606, respectively. This equality signal is passed by a six-input OR gate 506 and resets the flip flop 501. This disables the unijunction oscillator 502 before it produces its first pulse so that the binary counter output remains 0000. Output of the binary counter is the output 24 of means 14 and indicates the number of film frames to be skipped; in this case zero frames to be skipped.

If no outputs of OR Gates 301 to 306 are 0000, there will be no equality outputs from comparators 601 to 606 and the unijunction oscillator 502 will increment the binary counter 500 to 0001. The incrementing of the counter will continue and input to the comparators 601 to 606. When the increasing count from the counter 500 reaches the value of the lowest selected answer code value from OR Gates 301 to 306, the respective comparator will produce an equality signal to again terminate counter operation via operation of OR gate 506 to reset flip flop 501 and disable the oscillator 502, thereby producing the desired lowest-number skip command output 24 from the means 14, among the several chosen-answer skip-code number values.

What is claimed is:

1. An automatic self-administered interrogating apparatus comprising,
    film strip means for visually presenting a series of image frames at a viewing station, at least many of said image frames containing multiple answers viewable simultaneously at such station, and each such frame having an identification code affiliated with it, together with frame-count-advance codes respective to said answers,
    answer selection means operable to indicate choice of any one, several, or all of the aforesaid answers,
    recording means for storing said identification code and answer-choice information from said answer selection means,
    frame-count-advance selection means essentially comprising a bit-polarity-dominant logic circuitry for selecting frame-count-movement information from among the codes of the chosen answers, and
    means for effecting advancing movement of said film strip means according to such frame-count-movement information selection.

2. An automatic self-administered interrogating apparatus comprising,
    film strip means for visually presenting a series of image frames at a viewing station,
    at least many of said image frames containing multiple answers viewable simultaneously at such station, and each such frame having an identification code affiliated with it, together with frame-count-advance codes respective to said answers,
    answer selection means operable to indicate choice of any one, several, or all of the aforesaid answers,
    recording means for storing said identification code and answer-choice information from said answer selection means,
    frame-count-advance selection means essentially comprising last-answer-entry-recognizing circuitry for selecting frame-count-movement information from among the codes of the chosen answers, and
    means for effecting advancing movement of said film strip means according to such frame-count-movement information selection.

3. An automatic self-administered interrogating apparatus comprising,
    film strip means for visually presenting a series of image frames at a viewing station,
    at least many of said image frames containing multiple answers viewable simultaneously at such station, and each such frame having an identification code affiliated with it, together with frame-count-advance codes respective to said answers,
    answer selection means operable to indicate choice of any one, several, or all of the aforesaid answers,
    recording means for storing said identification code and answer-choice information from said answer selection means,
    frame-count-advance selection means essentially comprising lowest-selected-answer-code-number-determining logic circuitry for selecting frame-count-movement information from among the codes of the chosen answers, and
    means for effecting advancing movement of said film strip means according to such frame-count-movement information selection.

* * * * *